US008048457B2

(12) United States Patent
McNeff et al.

(10) Patent No.: US 8,048,457 B2
(45) Date of Patent: Nov. 1, 2011

(54) SAPONIN AND PRESERVATIVE COMPOSITIONS AND METHODS

(75) Inventors: Larry C. McNeff, Anoka, MN (US); Clayton V. McNeff, Andover, MN (US); Peter G. Greuel, Anoka, MN (US); Ryan Mass, Arlington, KS (US)

(73) Assignee: Sartec Corporation, Anoka, MN (US)

( * ) Notice: Subject to any disclaimer, the term of this patent is extended or adjusted under 35 U.S.C. 154(b) by 400 days.

(21) Appl. No.: 11/737,024

(22) Filed: Apr. 18, 2007

(65) Prior Publication Data

US 2007/0243269 A1 Oct. 18, 2007

Related U.S. Application Data

(60) Provisional application No. 60/745,018, filed on Apr. 18, 2006.

(51) Int. Cl.
*A61K 36/48* (2006.01)
*A61K 36/00* (2006.01)
*A01N 43/40* (2006.01)

(52) U.S. Cl. .................. 424/757; 424/725; 514/277

(58) Field of Classification Search .................. None
See application file for complete search history.

(56) References Cited

U.S. PATENT DOCUMENTS

| | | | |
|---|---|---|---|
| 4,388,327 A | 6/1983 | Cummins | |
| 5,139,779 A | 8/1992 | McNeff | |
| 5,219,596 A | 6/1993 | Smith et al. | |
| 5,240,727 A | 8/1993 | McNeff | |
| 5,279,838 A | 1/1994 | McNeff | |
| 5,496,571 A | 3/1996 | Blagdon et al. | |
| 5,518,750 A | 5/1996 | McNeff | |
| 5,891,491 A | 4/1999 | Owens et al. | |
| 6,017,564 A | 1/2000 | Owens et al. | |
| 6,733,759 B2 | 5/2004 | Ivey et al. | |
| 6,783,792 B2 * | 8/2004 | McDaniel et al. | 426/623 |
| 6,824,800 B1 | 11/2004 | Mitsuya et al. | |
| 6,955,831 B2 * | 10/2005 | Higgs et al. | 426/630 |
| 7,288,275 B2 * | 10/2007 | Axelrod et al. | 426/473 |
| 7,416,742 B2 | 8/2008 | McNeff et al. | |
| 2003/0092145 A1 * | 5/2003 | Jira et al. | 435/173.3 |
| 2006/0024387 A1 | 2/2006 | McNeff et al. | |
| 2006/0073194 A1 | 4/2006 | Taylor, Jr. et al. | |
| 2006/0188549 A1 * | 8/2006 | Block et al. | 424/442 |
| 2007/0071849 A1 | 3/2007 | McNeff | |
| 2007/0243269 A1 | 10/2007 | McNeff et al. | |
| 2007/0275152 A1 * | 11/2007 | Cook et al. | 426/630 |
| 2008/0145457 A1 | 6/2008 | McNeff et al. | |
| 2008/0274211 A1 | 11/2008 | McNeff et al. | |

FOREIGN PATENT DOCUMENTS

WO WO 2005/034645 * 4/2005

OTHER PUBLICATIONS

Han et al. J. Animal Sci. 2002. vol. 80, pp. 1117-1123.*

Cheeke, P. R., "Actual and potential applications of *Yucca schidigera* and *Quillaja saponaria* saponins in human and animal nutrition", *Proc. Am. Soc. Anim. Sci.*, 1999 (www.asas.org/symposia/proceedings/0909.pdf) 2000.
Fahmy, Wael G. et al., "Effect of Defaunation and Amino Acid Supplementation on Growth and Amino Acid Balance in Sheep", Aug. 5, 1998.
Francis, George et al., "The biological action of saponins in animal systems: a review.", *Br. J. Nutr.* 88(6) 2002 , 587-605.
Goodall, S. R. et al., "Rumensin with and without Sarsaponin for Finishing Feedlot Steers", *Col. Agr. Exp. Station No. 700* 1981.
Goodall, S. R. et al., "Sarsaponin effects upon ruminal VFA concentrations and weight gain of feedlot cattle", *J. Anim. Sci.* 49 1979 , 377-382.
Goodall, Richard S. et al., "Sarsaponin in Beef Cattle Rations", *Beef Nutrition Research* 1978, 9-10.
Goodall, S. R. et al., "The Effect of Sarsaponin with and without Rumensin in High-Energy Diets", *Col. Agr. Exp. Station No. 700* 1981.
Hristov, Alexander N. et al., "Effect of *Yucca schidigera* on ruminal fermentation and nutrient digestion in heifers", *J. Anim Sci.* 77 1999 , 2554-2563.
Klita, P. T. et al., "Effects of alfalfa root saponins on digestive function in sheep", *J. Animal Sci.* 74 1996 , 1144-1156.
Koenig, K. M. et al., "Effects of protozoa on bacterial nitrogen recycling in the rumen", *J. Anim Sci.* 78 2000 , 2431-2445.
Krumsiek, C. L. et al., "Agrado for Finishing Cattle: Effects on Performance, Carcass Measurements", *Oklahoma State University Department of Animal Science 1998 Animal Science Research Report* www.ansi.okstate.edu/research/1998rr/13.html 1998 , 64-68.
Lila, Z. A. et al., "Effect of Sarsaponin on Ruminal Fermentation with Particular Reference to Methane Production in Vitro", *J. Dairy Sci.* 86 2003 , 3330-3336.
Lu, C. D. et al., "Alfalfa saponins affect site and extent of nutrient digestion in ruminants", *J. Nutr.* 117 1987 , 919-927.
Mendoza, G. D. et al., "Influence of ruminal protozoa on site and extent of starch digestion and ruminal fermentation", *J. Anim Sci.* 71 1993 , 1572-1578. Navas-Camacho, Alberto et al., "Effect of reducing the rumen ciliate protozoa population by feeding saponin-containing plants on rumen function of sheep fed on wheat straw", *Arch. Latinoam. Prod. Anim.* 5(Supp. 1) 1997 , 98-101.
Rush, Ivan et al., "Grain Tempering Agent (SarTemp) for Corn in Finishing Rations", *Beef Cattle Report* 1993 , 63-64.
Unknown, et al., "Sevarin . . . with Sarsaponin gets 'em from feedlot to market faster, more profitably.", *Advertisment brochure by Distributors Processing Inc.* 1982 , 4.

(Continued)

*Primary Examiner* — Christopher R. Tate
(74) *Attorney, Agent, or Firm* — Pauly, DeVries Smith & Deffner, L.L.C.

(57) ABSTRACT

The invention is related to methods and compositions for improving feeding and/or production characteristics in animals. In an embodiment, the invention includes a method for improving feeding characteristics of an animal including administering a first composition comprising an effective amount of saponins to the animal, and administering a second composition comprising an effective amount of a preservative to the animal. In an embodiment, the invention includes a method for improving production characteristics of an animal including administering a first composition comprising an effective amount of saponins to the animal, and administering a second composition comprising an effective amount of a preservative to the animal.

8 Claims, No Drawings

OTHER PUBLICATIONS

Valdez, F. R. et al., "Effect of Steroidal Sapogenins on Ruminal Fermentation and on Production of Lactating Dairy Cows", *J. Dairy Sci. 69* 1986, 1568-1575.

Wallace, R. J. et al., "Influence of *Yucca shidigera* Extract on Ruminal Ammonia Concentrations and Ruminal Microorganisms", *Appl. Environ. Microbiol.* 60(6) Jun. 1994, 1762-1767.

Wang, Y. et al., "Effects of *Yucca schidigera* extract on fermentation and degradation of steroidal sponins in the rumen simulation technique (RUSITEC)", *Animal Feed Sci. Technol. 74* 1998, 143-153.

Wilson, R. C. et al., "Effects of *Yucca shidigera* Extract and Soluble Protein on Performance of Cows and Concentrations of Urea Nitrogen in Plasma and Milk", *J. Dairy Sci. 81* 1998, 1022-1027.

"Safe Water System—Effect of Chlorination on Inactivation Selected Pathogens", *Appl. Environ. Microbiol.* 1988, 54(12): 3023-33.

"File History for co-pending U.S. Appl. No. 12/251,833, "Saponin and Preservative Compositions for Reduction of Protozoa," (160 pages)".

"Non-Final Office Action mailed Dec. 29, 2010 in co-pending U.S. Appl. No. 12/251,833, "Saponin and Preservative Compositions for Reduction of Protozoa" (10 pages).", Dec. 2010.

"Response to Non Final Office Action filed Apr. 29, 2011", in co-pending U.S. Appl. No. 12/251,833, filed with USPTO Oct. 15, 2008 (8 pages), Apr. 2011.

* cited by examiner

SAPONIN AND PRESERVATIVE COMPOSITIONS AND METHODS

RELATED APPLICATIONS

This application claims the benefit of U.S. Provisional Application No. 60/745,018, filed Apr. 18, 2006, and titled "Saponin and Preservative Compositions and Methods", the contents of which is herein incorporated by reference.

FIELD OF THE INVENTION

The invention is related to methods and compositions for improving feeding and/or production characteristics in animals. More specifically, the invention is related to methods and compositions for increasing feeding and/or production characteristics in animals using a saponin composition in combination with a preservative.

BACKGROUND OF THE INVENTION

Of the total costs involved with livestock production, feed costs are the most significant. Accordingly, maximizing feeding efficiency and productive output are of the utmost importance to the livestock industry.

Different techniques have been utilized in order to improve feeding efficiency and/or productive output in animals including the use of various feed additives. Examples of feed additive techniques can be found in U.S. Pat. No. 5,496,571 (Blagdon et al.), U.S. Pat. No. 5,219,596 (Smith et al.), and U.S. Pat. No. 4,388,327 (Cummins). However, many feed additives are insufficiently beneficial.

Accordingly, a need exists for methods and compositions that will improve feeding characteristics such as feeding efficiency and/or productive output in animals.

SUMMARY OF THE INVENTION

The invention is related to methods and compositions for improving feeding and/or production characteristics in animals. In an embodiment, the invention includes a method for improving production characteristics of an animal including administering a first composition comprising an effective amount of saponins to the animal, and administering a second composition comprising an effective amount of a preservative to the animal. In an embodiment, the invention includes a method for improving feeding characteristics of an animal including administering a first composition comprising an effective amount of saponins to the animal, and administering a second composition comprising an effective amount of a preservative to the animal.

The above summary of the present invention is not intended to describe each discussed embodiment of the present invention. This is the purpose of the detailed description that follows.

DETAILED DESCRIPTION OF THE INVENTION

Embodiments of the present invention include methods and compositions for improving feeding characteristics of animals and/or improving production characteristics of animals including administering an effective amount of saponins and administering an effective amount of a preservative.

Saponins are natural plant surfactants that occur in over 500 different plant species belonging to some 80 different families. They are generally recognized by their strong foaming action when placed in water, which has made them especially useful in the manufacture of foods, beverages, shampoos, wetting agents and pharmaceuticals.

Saponins are classified as surfactants because they have both lipophilic and hydrophilic "regions". Thus, the surfactant activity of saponins is a result of both fat-soluble and water-soluble moieties in the same molecule. The lipophilic region may be a steroid, triterpene, or alkaloid, and is termed a sapogenin. The hydrophilic "region" contains one or more water-soluble carbohydrate side chains. The structural complexity of saponins is derived largely from the carbohydrate portion of the molecule due to the many different types of possible side chain carbohydrates, such as glucose, xylose, galactose, pentose or methylpentose, which may have different connectivity and/or anomeric configuration. Saponins have an antiprotozoal activity attributed to the saponin's ability to interact with cholesterol in protozoal cell membranes and cause cell lysis.

Ethoxyquin (1,2-dihydro-6-ethoxy-2,2,4-trimethylquinoline; CAS No. 91-53-2) is an antioxidant and is one example of a preservative that can be used in embodiments of the invention. Ethoxyquin has also been used as an animal feed additive. Animal feed uses of ethoxyquin include: (1) to retard oxidation of carotene, xanthophylls and Vitamins A and E in animal feed and fish food, (2) to retard oxidation of Vitamin E and carotene in dehydrated forage crops and (3) to retard organic peroxides in canned pet food.

Other preservatives can include: ascorbic acid, ascorbyl palmitate, benzoic acid, butylated hydroxyl anisole (BHA), butylated hydroxytoluene (BHT), calcium ascorbate, calcium proprionate, calcium sorbate, citric acid, dilauryl thiodipropionate, distearyl thiodiproprionate, erythrobic acid, formic acid, methylparaben, potassium bisulfite, potassium metabisulfite, potassium sorbate, propionic acid, propyl gallate, propylparaben, resin guaiac, sodium ascorbate, sodium benzoate, sodium bisulfite, sodium metabisulfite, sodium nitrite, sodium propionate, sodium sorbate, sodium sulfite, sorbic acid, stannous chloride, sulfur dioxide, tertiary butyl hydroquinone (TBHQ), thiodipropionic acid, and tocopherols.

The methods and compositions of the invention can be used for the treatment of animals, including bovine, fowl, porcine, ovine, and equine species. By way of example, the methods and compositions of the invention can be used for the treatment of cattle, chickens, turkeys, ducks, quail, geese, pigs, and sheep. In a specific embodiment, the methods and compositions of the invention can be used for the treatment of ruminants.

In an embodiment, the saponin containing composition used in accordance with the invention comprises at least 0.1% by weight saponins as measured by HPLC. In an embodiment, the saponin containing composition used in accordance with the invention comprises at least 0.5% by weight saponins as measured by HPLC. In a particular embodiment, the saponin containing composition used in accordance with the invention comprises at least 1.0% by weight saponins as measured by HPLC. It is believed that the effects of the composition are related to the total amount of saponins present. Thus, one of skill in the art will appreciate that if a certain amount of saponins is desired it can be achieved either through varying the volume of a certain concentration composition administered, varying the concentration of a certain volume of a composition, or both.

Saponins useful in the present invention may also be extracted from plants of the family: Lillaecae, genus: *Yucca*, such as *Yucca schidigera*. *Yucca* derived saponins generally have steroidal sapogenins. Sarsasapogenin is the major sapogenin found in the *Yucca schidigera* plant. Saponins useful in the present invention can also extracted from plants of the family: Amaryllidaccae, genus: *Agave*, which grows extensively in the southwestern United States and in Mexico. Additional sources of saponins can include extracts of soybeans, fenugreek, peas, tea, yams, sugar beets, alfalfa, asparagus, aloe, vanilla, zhimu, *Sapindus saponaria*, citrus fruits (limonoid saponins) as well as from *Quillaja saponaria* bark. Saponins can be extracted from plant materials in accordance with techniques well-known by those of skill in the art.

Many saponin containing compositions are available commercially. An exemplary liquid composition containing saponins is sold under the trademark SARTEMP® by SarTec Corporation of Anoka, Minn. It can prepared by blending an aqueous extract of the plants of the family: Lillaecae, genus: *Yucca*, or other appropriate *Yucca* plants containing 10% solids with antifreeze agents such as calcium chloride, propylene glycol, and the like, to depress the freezing point to −30° F. The final concentration of *Yucca* soluble solids is 8.25%. The physical and chemical data of SARTEMP® are as follows: Bulk density—10.4 lbs. per gallon; Color—Dark brown; Freezing Point—−30° F.; Saponin—at least 390 grams per gallon (3 grams per ounce); pH—5.5-6.0; Total solids—33%; Water—67%.

Compositions in accordance with embodiments of the invention can include various other additives. By way of example, compositions can also include components such as, water, propylene glycol, Vitamin E (as di-alpha-tocopheryl acetate), Vitamin A Propionate, Vitamin A Palmitate, Vitamin B1, Vitamin B2, Vitamin B6, Vitamin B12, D-Activated Animal Sterol (source of Vitamin D3), yeast components, dried egg solids, dried casein, and dried whey.

The typical saponin content that naturally occurs in *Yucca* plants is from 0.1-2% saponins by weight. *Yucca* extracts can be derived by extracting yucca powder with an aqueous solution that may or may not contain some fraction of organic solvent such as methanol, ethanol, propanol, butanol, or the like.

Commercially available *Yucca* extracts can have a total solids content usually in the range from 5-50%. The saponin content of a typical 50 brix (50% solids by weight) yucca extract is usually in the range of about 1-2% saponins by weight as measured by HPLC analysis. Another method of measuring total saponin content is the extraction of all soluble components into a butanol extract followed by gravimetric analysis of the compounds dissolved in the butanol fraction. Measuring saponin content by the butanol extract method typically results in higher numbers than the more advanced HPLC method. Accordingly, the typical 50 brix (50% solids by weight) yucca extract is usually in the range of about 5-20.0% saponins content by weight as measured by the butanol extract method.

Saponin containing compositions can also be formulated as dry powder. Such dry formulations are available commercially (SARSTART D®, SARSTART DSC®, SarTec Corporation, Anoka, Minn.). Dry powder formulations of saponin containing compositions may be added to the feed ration via a micro-ingredient machine or added to a feed mix truck and mixed thoroughly to assure even distribution in the feed. By way of example, a dry formulation can be added at a rate of 0.25 gram to 10 grams per head per day rate.

Saponin containing compositions in accordance with the invention may be in liquid or dry forms. By way of example, a saponin containing plant extract may be dried into a powder form. In this form, the saponin containing composition may be administered to an animal as a pill or bolus, or mixed in with other components such as a feed ration. Saponin containing plant extract may also be in a solution with an amount of a carrier liquid such as water. In this form, the saponin containing composition may be administered to an animal as a liquid drench.

Saponin containing compositions may be administered to an animal as a single dose. Saponin containing compositions may also be administered to an animal in multiple doses. For example, an animal may receive an initial dose and then receive subsequent maintenance doses in lesser amounts. An animal may receive multiple doses of a saponin containing composition in one day, or may receive multiple doses over multiple days.

Animals can be treated with a saponin containing composition in an amount that is effective to improve the feeding characteristics of an animal and/or improve the production characteristics of an animal in comparison to an untreated control animal. Production characteristics can include carcass quality grades, yield grades, average daily gain, milk production, and the like. In an embodiment, the amount of saponins in a dose of a saponin containing composition is at least about 5 milligrams. In an embodiment, the amount of saponins in a dose of a saponin containing composition is less than about 10 grams. In an embodiment, the amount of saponins in a dose of a saponin containing composition is about 5 mg to 10 grams.

Preservative compositions may be in liquid or dry forms. The preservative composition may be administered to an animal as a pill, bolus, drench, or mixed in with other components such as a feed ration.

Animals can be treated with a preservative composition in an amount that is effective to improve the feeding characteristics of an animal and/or improve the production characteristics of an animal in comparison to an untreated control animal. For example, an amount of ethoxyquin equal to between about 10 and about 150 ppm of the animals feed ration is administered. In some instances, an amount of ethoxyquin equal to about 50 ppm of the animals feed ration can be administered. In some embodiments, an amount of ethoxyquin equal to about 100 ppm of the animals feed ration is administered. In other embodiments, an amount of ethoxyquin equal to about 150 ppm of the animals feed ration is administered.

Administration of the saponin composition may be at the same time as administration of the preservative composition or at a different time. In an embodiment, a saponin containing composition is administered at the same time as ethoxyquin. In an embodiment, a composition comprising both saponins and ethoxyquin are administered. In an embodiment, a saponin containing composition is administered at least one hour before ethoxyquin is administered.

Aspects of the present invention may be better understood with reference to the following examples. These examples are intended to be representative of specific embodiments of the invention, and are not intended as limiting the scope of the invention.

EXAMPLE 1

Effects of Saponin and Ethoxyquin Composition on Production Characteristics of Steers Three hundred and sixty cross-bred Holstein steers were selected from a single source dairy in New Mexico. These cattle were fed from an average incoming weight of 300 pounds to a trial start weight of 914 pounds. When the cattle reached the trail start weight they were split randomly into control and test pens. The control cattle weighed on average 888 pounds. The test cattle weighed on average 940 pounds.

After sorting, both the test and control cattle received the normal finishing ration (80% rolled corn, hay and supplement). The supplement fed to all cattle (test and control) during the trial contained Rumensin and Tylan.

In addition to the normal diet, the test cattle received 7.0 grams of a test composition per head per day (split up over 2 feedings per day) mixed directly into the ration. The test composition comprised approximately 2.5 wt. % of a *Yucca Schidigera* powder/extract. The test composition also included 21.1 wt. % ethoxyquin (obtained from Novus International Inc. as AGRADO powder). The test composition is available commercially as SARCHOICE, from SarTec Corporation, Anoka, Minn. The test composition was administered with a micro-additive machine. All cattle received normal vaccinations and were implanted and re-implanted per schedule. The trial was conducted for 109 days. At the end of the trial period all cattle were harvested.

An exemplary production characteristic is the grading of meat obtained from harvested steers. As such, to evaluate the effects of the test composition on the steers, the harvested carcasses were graded according to standard USDA beef carcass grading guidelines for both quality grade (with Prime representing the highest quality and Choice representing the second highest quality) and yield grade (1-5, with Yield Grade 1 representing the highest degree of cutability). The results are shown in Tables 1 and 2 below.

TABLE 1

| Quality Grade | Treatment (%) | Control (%) |
| --- | --- | --- |
| Prime | 0.0 | 0.0 |
| Choice | 48.0 | 42.3 |
| Select | 37.0 | 42.1 |
| Dark Cutter | 3.0 | 3.3 |
| Ungraded | 12.0 | 12.3 |

TABLE 2

| Yield Grade | Treatment (%) | Control (%) |
| --- | --- | --- |
| 1 | 11.0 | 10.0 |
| 2 | 68.0 | 71.0 |
| 3 | 20.5 | 19.0 |
| 4 | 0.5 | 0.0 |
| 5 | 0.0 | 0.0 |

The data shows that administration of the test composition, including saponins and ethoxyquin, caused a substantial increase in the percentage of carcasses graded as "Choice" in comparison to the otherwise similar control groups of steers. Specifically, the percentage of carcasses graded as "Choice" improved from 42.3% to 48%, or an increase of over 13%. As the economic value of beef graded as "Choice" is uniformly higher than beef graded as "Select", this increase in the percentage graded as "Choice" represents a significant improvement in the production characteristics of the steers. Dry matter intake (DMI) for both groups of steers was also monitored over the course of the trial. It was found that the test group had a daily DMI that was approximately 2.4% higher, on average, than the control group of steers.

The invention claimed is:

1. A method for improving production characteristics of an animal comprising:
improving average quality grading of animal carcasses by administering the effective amount of a composition to a ruminant daily, the composition comprising about 2.5 wt. % of a yucca extract, and about 20 wt. % of ethoxyquin, wherein the yucca extract comprises saponins.

2. The method of claim 1, wherein improving production characteristics comprises increasing the percentage of carcasses graded as choice.

3. The method of claim 1, wherein improving production characteristics comprises increasing the percentage of carcasses graded as choice by at least about ten percent.

4. The method of claim 1, wherein the ruminant is *Bos taurus*.

5. The method of claim 1, wherein the ruminant is a steer.

6. The method of claim 1, wherein the composition comprises 2.5 wt. % of the yucca extract.

7. The method of claim 1, wherein the composition comprises 21.1 wt. % of the ethoxyquin.

8. The method of claim 1, wherein the saponins comprise sarasaponins.

* * * * *